(12) United States Patent
Kirwan, Jr.

(10) Patent No.: US 6,228,084 B1
(45) Date of Patent: May 8, 2001

(54) ELECTRO-SURGICAL FORCEPS HAVING RECESSED IRRIGATION CHANNEL

(75) Inventor: Lawrence T. Kirwan, Jr., Pembroke, MA (US)

(73) Assignee: Kirwan Surgical Products, Inc., Marshfield, MA (US)

( * ) Notice: Subject to any disclaimer, the term of this patent is extended or adjusted under 35 U.S.C. 154(b) by 0 days.

(21) Appl. No.: 09/286,694

(22) Filed: Apr. 6, 1999

(51) Int. Cl.⁷ ................................................ A61B 18/18
(52) U.S. Cl. ................................................ 606/52; 606/51
(58) Field of Search ............................. 606/51, 52, 206, 606/207

(56) References Cited

U.S. PATENT DOCUMENTS

| | | | |
|---|---|---|---|
| 4,567,890 | * | 2/1986 | Ohta et al. ........................ 606/51 |
| 5,217,460 | * | 6/1993 | Knoepfler ......................... 606/51 |
| 5,603,712 | * | 2/1997 | Koranda et al. .................. 606/51 |
| 5,746,739 | * | 5/1998 | Sutter ................................. 606/51 |

* cited by examiner

*Primary Examiner*—Michael Peffley
(74) *Attorney, Agent, or Firm*—Weingarten, Schurgin, Gagnebin & Hayes LLP

(57) ABSTRACT

An electro-surgical forceps has a recessed irrigation channel. The forceps includes a pair of blades mounted in a cap portion. A groove is recessed in the inner surface of a first blade of the pair of blades. Tubing is disposed in the groove. The tubing terminates at a location spaced from the termination of the groove to provide an outlet from the groove. The depth of the groove and the outer diameter of the tubing are selected such that the tubing is substantially recessed below the inner surface of the first blade sufficiently that a surgeon's view of the inner faces of the tips of the blades is not obstructed by the irrigation channel. The blades may be covered with an insulating material if desired.

10 Claims, 2 Drawing Sheets

ELECTRO-SURGICAL FORCEPS HAVING RECESSED IRRIGATION CHANNEL

CROSS REFERENCE TO RELATED APPLICATIONS

N/A

STATEMENT REGARDING FEDERALLY SPONSORED RESEARCH OR DEVELOPMENT

N/A

BACKGROUND OF THE INVENTION

Electro-surgical forceps have a pair of resilient blades that are used for grasping and coagulating tissue. The blades may be held together by molding their ends opposite the tips within a cap. The forceps may be monopolar or bipolar. In monopolar forceps, the blades are welded or otherwise joined to form an electrode in electrical communication with an electrical generator. Current flows from the active electrode through the patient's tissue to a dispersive electrode in contact with the patient's skin (which may be at some distance from the forceps) and back to the generator. In bipolar forceps, each blade of the pair comprises an electrode in communication with an electrical generator.

In some forceps, an irrigation channel is formed along the length of one of the blades. See FIG. 5. The channel is typically formed from a length of metal tubing which is attached to the inside surface of the blade in a suitable manner, such as with an adhesive, brazing, or welding. The tubing includes an outlet near the tip of the blades and an entrance segment that is affixed within the cap. An inlet is provided at the beginning of the entrance segment. An irrigation fluid, such as saline solution, flows through the channel and out the outlet near the tip of the blades to flush bits of tissue or blood away from the area where the surgeon is working.

BRIEF SUMMARY OF THE INVENTION

The present invention provides an electro-surgical forceps having a recessed irrigation channel in one of the pair of blades. The recessed irrigation channel provides the surgeon with an unobstructed view of the tips of the blades. Additionally, the recessed channel allows the blades to close completely at their tips.

More particularly, the electro-surgical forceps comprise an insulated cap portion, at least one terminal extending from and fixed to the cap portion, and a pair of blades. Each blade is generally elongated and has an inner surface, an outer surface, and a tip portion. Each blade also has an opposite end fixed within the cap portion. At least one of the blades is electrically connected to the at least one terminal within the cap portion.

The forceps includes an irrigation channel comprising a groove recessed in the inner surface of a first blade of the pair of blades. The groove extends along substantially the length of the first blade from an origination proximate the cap portion to a termination proximate the tip of the first blade. A length of tubing is disposed in the groove along substantially the length of the first blade. The tubing includes an inlet segment extending from an inlet in the cap portion to the origination of the groove. The tubing terminates at a location spaced from the termination of the groove to provide an outlet from the channel. The depth of the groove and the outer diameter of the tubing are selected such that the tubing is fully recessed below the inner surface of the first blade. An inlet in the cap portion is configured to connect to a source of irrigation fluid. The tubing inlet segment is in fluid communication with the inlet in the cap portion.

A spacer post may be provided to extend from the inner surface of a second blade of the pair of blades. An insulating coating may be disposed over the blades and the irrigation channel.

BRIEF DESCRIPTION OF THE DRAWINGS

The invention will be more fully understood from the following detailed description taken in conjunction with the accompanying drawings in which.

DETAILED DESCRIPTION OF THE INVENTION

Figure 1:
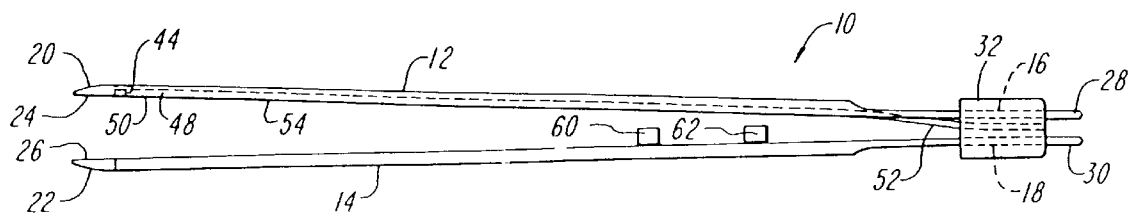
FIG. 1 is a plan view of electro-surgical forceps having a recessed irrigation channel according to the present invention.
Figure 2:
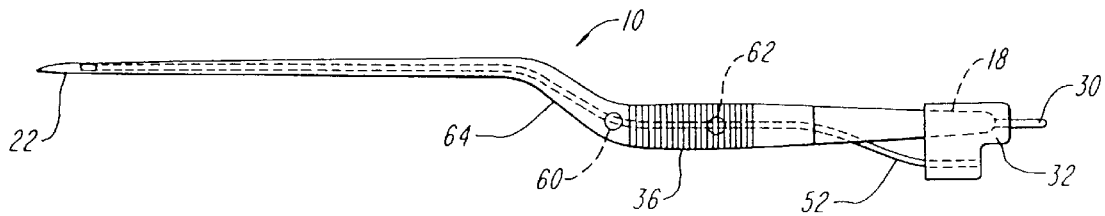
FIG. 2 is a side view of the electro-surgical forceps of FIG. 1.
Figure 3:
FIG. 3 is an end view of the electro-surgical forceps of FIG. 1.
Figure 4:
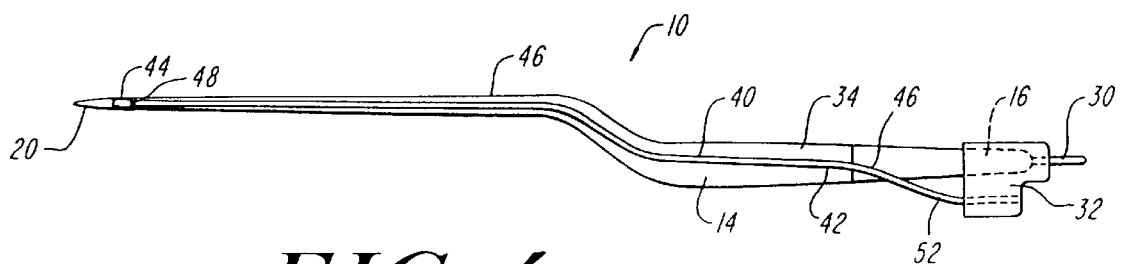
FIG. 4 is a side view of the inner surface of a blade of the electro-surgical forceps of FIG. 1.
Figure 5:
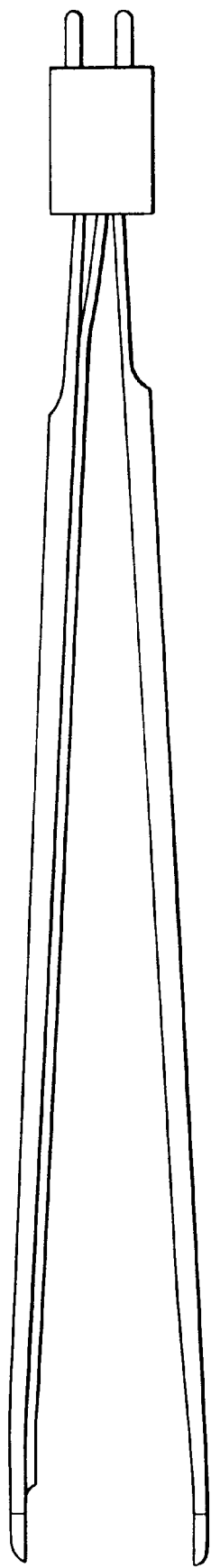
FIG. 5 is a plan view of prior art electro-surgical forceps.

Referring to FIGS. 1 through 4, a bipolar forceps 10 has first and second blades or electrode members 12, 14. Each of the blades is elongated and extends from a first end 16, 18 to a second end or tip portions 20, 22. The blades are generally flat to have a greater width than depth, such that the tip portions are configured for gripping tissue between opposed inner faces 24, 26. The first ends 16, 18 are electrically connected in any suitable manner, such as by crimping, welding, or soldering, to terminal pins 28, 30. The first ends along with the terminal pins are encapsulated using an epoxy-based material or otherwise mounted within an insulating cap portion 32. The blades 12, 14 may be insulated with an insulating material 34 along most of their length from the cap portion 32 to a location close to the tip portions. Serrated finger grips 36 may be formed in each blade member to aid the physician in gripping the forceps during use. A plating of an electrically and thermally conductive biocompatible material such as gold may be provided on the tip portions 20, 22.

A groove 40 is machined or ground along most of the length of one 12 of the blades. The groove is shown in the first blade 12 in the figures; however, it could also be formed in the second blade 14, if desired. The groove begins at a location 42 near the cap portion 32 and terminates at a location 44 near the tip portion 20 of the blade. A length of tubing 46 is placed in the groove. The tubing terminates at a location 48 spaced slightly from the termination of the groove to provide an outlet 50 from the irrigation channel for fluid flowing through the tubing. An inlet or beginning segment 52 of the tubing is encapsulated in the cap portion 32. The inlet segment extends from the cap portion to the beginning location 42 of the channel in the first blade.

The tubing 46 is preferably formed of a suitable metal material, such as stainless steel, nickel, or titanium. The metal may be conductive. Alternatively, the tubing may be formed of other materials, such as a plastic material. Preferably, the tubing is sufficiently flexible to move with movement of the blades by a surgeon during use. It may also be sufficiently flexible to be formed to fit within the configuration of the groove, or if of a stiffer material, it may be preformed to the configuration of the groove. The tubing is fixed within the groove in any suitable manner such that it cannot be readily removed from the groove. For example, the tubing may be epoxied, brazed, or welded into the groove.

The depth of the groove 40 and the outer diameter of the tubing 46 are selected such that the tubing is substantially recessed below the inner surface 54 of the blade 12. The tubing is recessed sufficiently such that the irrigation channel does not obstruct the surgeon's view of the inner faces 24, 26 of the tip portions 20, 22 of the blades. Additionally, the tubing is recessed sufficiently to allow the blades to close completely at their tips. Preferably, the tubing is recessed fully below the inner surface of the blade.

As noted above, the blades may be encapsulated in an insulating material 34 such as a plastic material capable of withstanding the high temperatures generated during use. The insulation may be formed in any suitable manner, such as by spraying on a liquid which dries to form a solid coating. The tip portion of the blade members and the outlet 50 of the irrigation channel are left uninsulated. The insulation is typically 0.010 to 0.015 inches thick. The tip may be plated with a thin layer of an electrically and thermally conducting, biocompatible material, such as gold or rhodium, using conventional plating processes. Preferably, the plating layer provides good electrical and thermal conductivity. Other electrically and thermally conductive materials that are biocompatible with human tissue may be used.

If desired a post or pair of posts 60, 62 may be provided on the inner surface of one of the blades. The post prevents the blades from closing completely at the tips, which may be desirable in some applications. The posts may be formed in any suitable manner, and may be fixed to the blade by, for example, epoxy.

Although described in conjunction with bipolar forceps, it will be appreciated that the irrigation channel of the present invention can be used with monopolar forceps. Similarly, the blades are shown with an offset 64 formed therein; however, the present invention may also be employed with straight blades, as are known in the art.

The invention is not to be limited by what has been particularly shown and described, except as indicated by the appended claims.

I claim:

1. An electro-surgical forceps comprising:

an insulated cap portion;

at least one terminal extending from and fixed to the cap portion;

a pair of blades, each blade being generally elongated and having an inner surface, an outer surface, and a tip portion and having an end opposite the tip portion fixed within the cap portion, at least one of the blades electrically connected to the at least one terminal within the cap portion; and an irrigation channel comprising:

a groove recessed in the inner surface of a first blade of the pair of blades, the groove extending continuously along substantially the length of the first blade from an origination proximate the cap portion to a termination proximate the tip of the first blade;

tubing disposed in the groove continuously along substantially the length of the first blade, the tubing including an inlet segment extending from an inlet in the cap portion to the origination of the groove, the tubing terminating at a location spaced from the termination of the groove to provide an outlet from the irrigation channel, the depth of the groove and the outer diameter of the tubing selected such that the tubing is substantially recessed below the inner surface of the first blade to provide a surgeon with an unobstructed view of inner faces of the tip portions of the blades; and an inlet in the cap portion configured to connect to a source of irrigation fluid, the tubing inlet segment in fluid communication with the inlet in the cap portion.

2. The electro-surgical forceps of claim 1, wherein the tubing is recessed below the inner surface of the first blade sufficiently to allow the tip portions of the blades to close fully.

3. The electro-surgical forceps of claim 1, wherein the tubing comprises a metal material.

4. The electro-surgical forceps of claim 1, wherein the tubing comprises a plastic material.

5. The electro-surgical forceps of claim 1, wherein the tubing is sufficiently flexible to move with movement of the pair of blades.

6. The electro-surgical forceps of claim 1, further comprising at least one spacer post extending from the inner surface of a second blade of the pair of blades.

7. The electro-surgical forceps of claim 1, further comprising a pair of spacer posts extending from the inner surface of a second blade of the pair of blades.

8. The electro-surgical forceps of claim 1, further comprising an electrically and thermally conductive coating on the tip portion of each blade.

9. The electro-surgical forceps of claim 1, further comprising an insulating coating disposed over the blades and the irrigation channel.

10. The electro-surgical forceps of claim 1, wherein the depth of the groove and the outer diameter of the tubing selected such that the tubing is fully recessed below the inner surface of the first blade.

* * * * *